United States Patent
Devisetty

(10) Patent No.: US 11,299,439 B2
(45) Date of Patent: Apr. 12, 2022

(54) **MYCORRHIZAE AND/OR *BACILLUS AMYLOLIQUEFACIENS* LIQUID FERTILIZER COMPATIBLE FORMULATIONS**

(71) Applicant: Valent BioSciences LLC, Libertyville, IL (US)

(72) Inventor: Bala N. Devisetty, Buffalo Grove, IL (US)

(73) Assignee: VALENT BIOSCIENCES LLC, Libertyville, IL (US)

(*) Notice: Subject to any disclaimer, the term of this patent is extended or adjusted under 35 U.S.C. 154(b) by 206 days.

(21) Appl. No.: 16/837,058

(22) Filed: Apr. 1, 2020

(65) Prior Publication Data

US 2020/0308073 A1    Oct. 1, 2020

Related U.S. Application Data

(60) Provisional application No. 62/827,500, filed on Apr. 1, 2019.

(51) Int. Cl.
| | | |
|---|---|---|
| *C05F 11/08* | (2006.01) | |
| *A01G 7/06* | (2006.01) | |
| *C05G 5/20* | (2020.01) | |
| *C05G 5/23* | (2020.01) | |

(52) U.S. Cl.
CPC ............ *C05F 11/08* (2013.01); *A01G 7/06* (2013.01); *C05G 5/20* (2020.02); *C05G 5/23* (2020.02)

(58) Field of Classification Search
None
See application file for complete search history.

(56) References Cited

U.S. PATENT DOCUMENTS

| | | | |
|---|---|---|---|
| 10,238,103 B2 | 3/2019 | Devisetty et al. | |
| 2016/0355445 A1* | 12/2016 | Bobeck | C05G 3/90 |
| 2017/0008815 A1 | 1/2017 | Johnson | |
| 2017/0347663 A1 | 12/2017 | Huang et al. | |
| 2017/0347665 A1 | 12/2017 | Huang et al. | |
| 2018/0022657 A1* | 1/2018 | Devisetty | C05G 5/27 |
| | | | 71/27 |
| 2018/0022659 A1* | 1/2018 | Devisetty | C05F 11/08 |
| | | | 71/27 |
| 2018/0279621 A1 | 10/2018 | Sasakawa et al. | |
| 2019/0014788 A1* | 1/2019 | Sawant | C05G 5/23 |
| 2019/0124917 A1* | 5/2019 | Bobeck | C05G 3/90 |
| 2021/0106011 A1* | 4/2021 | Guan | A01N 63/22 |
| 2021/0127684 A1* | 5/2021 | Singh | C05G 3/70 |
| 2021/0345618 A1* | 11/2021 | Bloch | C12N 15/01 |

OTHER PUBLICATIONS

International Search Report and Written Opinion dated Jun. 11, 2020.

* cited by examiner

*Primary Examiner* — Wayne A Langel
(74) *Attorney, Agent, or Firm* — Wood, Phillips, Katz, Clark & Mortimer

(57) ABSTRACT

The present invention is directed to agricultural formulations containing mycorrhizae and/or *Bacillus amyloliquefaciens* that are compatible with liquid fertilizers. The present invention further relates to methods of improving plant growth by applying mycorrhizae and/or *Bacillus amyloliquefaciens* containing formulations to an area where a plant will grow.

17 Claims, 1 Drawing Sheet
(1 of 1 Drawing Sheet(s) Filed in Color)

US 11,299,439 B2

MYCORRHIZAE AND/OR *BACILLUS AMYLOLIQUEFACIENS* LIQUID FERTILIZER COMPATIBLE FORMULATIONS

FIELD OF THE INVENTION

The present invention is directed to an agricultural formulation containing Mycorrhizae and/or *Bacillus amyloliquefaciens* that is compatible in liquid fertilizer solutions. The present invention further relates to methods of improving plant growth by applying mycorrhizae and/or *Bacillus amyloliquefaciens* containing formulations to a plant or plant propagation material.

BACKGROUND OF THE INVENTION

Huge amounts of water and fertilizer are utilized across agricultural and landscaping practices. These practices, although readily accepted and necessary, lead to an exacerbation of water quantity and quality issues across the world. For example, agriculture uses about 70% of the accessible freshwater. The water that is not used may be contaminated by toxic chemicals found in fertilizers. Specifically, contamination of municipal water supplies by nitrates is dangerous to human health and increased phosphate content in rivers and streams leads to lower oxygen levels and possibly large-scale fish kill.

Mycorrhizae are symbiotic associations between fungi (i.e. mycorrhizal fungi) and the roots of plants. Mycorrhizal fungi are associated with greater than 90% of all land plants including crops, grasses and trees. Mycorrhizal fungi provide many important benefits to plants including enhanced absorption of water and nutrients from the soil, increased drought resistance, increased pathogen resistance and protection, enhanced plant health and vigor, minimized effects of external stress, and enhanced seedling growth. In turn, the external application of Mycorrhizal fungi to plants can lead to less irrigation and fertilization, which conserves water and reduces the amount of chemicals, such as nitrates and phosphorus, and micronutrients. Mycorrhizal fungi are most effective when introduced to the soil prior to seed germination or at early stages of plant root proliferation.

Current Mycorrhizae formulations include those developed by Mycorrhizal Applications, which produces liquid formulations and wettable powders as seed treatments and in-furrow formulations. However, these formulations only contain about 7,600 propagules ("ppg's") per mL for seed treatments, about 950 ppg's per mL for in-furrow formulations and about 280 ppg's per gram for wettable powders and have been known to clog spray nozzle screens as large as 50 mesh (300 micrometers). In the liquid formulations, propagules settle rapidly to the bottom of the packaged container. Uniform dosing or application is not guaranteed or certain for such rapidly settling formulations. Further, current Mycorrhizae formulations are not "application friendly" and lack physical stability and homogeneity with liquid fertilizers.

*Bacillus amyloliquefaciens* is a soil bacterium found in the root zone of many plants. *B. amyloliquefaciens* have a symbiotic relationship with the plants in which they stimulate producing plant growth promoting substances while feeding on organic compounds from the plant. *B. amyloliquefaciens* may also help in reducing the amount of fertilizer necessary to maximize growth and yield of commercial crops.

However, many of liquid bacterial and chemical agricultural formulations are not physically compatible with liquid fertilizers. This includes the commercially available Poncho®/VOTiVO® and DoubleNickle LC and those formulations disclosed in US2011/0033436A1, assigned to Bayer Intellectual Property GmbH and in U.S. Pat. Nos. 10,111,439 and 10,111,440 assigned to Valent BioSciences LLC.

Accordingly, there is a need to develop new Mycorrhizae and/or live *Bacillus amyloliquefaciens* formulations capable of delivering higher concentrations of Mycorrhizal fungi and/or live *B. amyloliquefaciens* while maintaining prolonged and efficient viability and non-dormant propagules, as well as improved physical stability and homogeneity not only in the packaged containers but also when combined in liquid fertilizers for in-furrow applications at or during planting.

SUMMARY OF THE INVENTION

The present invention is directed to agricultural formulations comprising:
an active ingredient selected from the group consisting of mycorrhizae, *Bacillus amyloliquefaciens* and a mixture thereof;
propylene glycol; and
a stabilizer selected from the group consisting of benzenesulfonic acid, decyl (sulfophenoxy)-disodium salt, benzenesulfonic acid oxybis(decyl)-disodium salt mixture, sodium mono- and di-decyl disulfonated diphenyl oxide, D-glucopyranose, oligomeric, C9-11-alkyl glycosides and a mixture thereof.

The present invention is further directed to methods of improving plant growth by applying the formulations of the present invention to a plant or an area where a plant will grow including plant root zones and furrows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
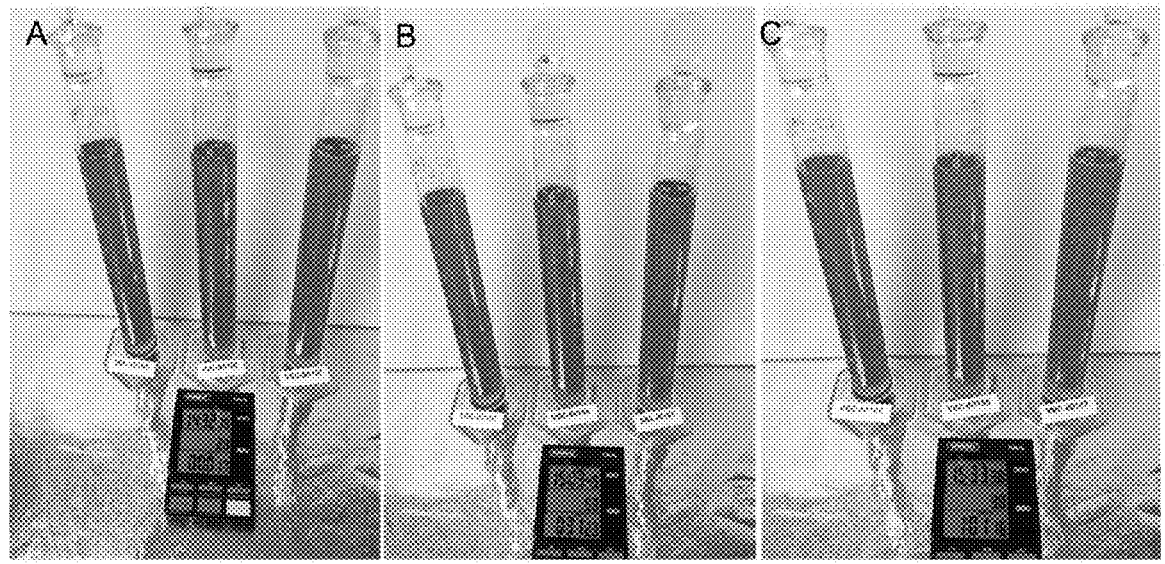
FIG. 1. Stability of formulations M1, M2 and M3 (left to right), at time 0 (A), 0.5 hours (B) and 1 hour (C).

The Applicant has unexpectedly discovered mycorrhizae and/or *Bacillus amyloliquefaciens* formulations that are stable at relatively high concentrations and are physically compatible with liquid fertilizers.

As used herein, the terms "Mycorrhiza" or "Mycorrhizae" refers to an organic material containing a Mycorrhizal fungus and the plant roots to which the Mycorrhizal fungus is symbiotically associated. The symbiotic association of the Mycorrhizal fungus to the plant roots may be either intracellular (i.e. arbuscular Mycorrhiza) or extracellular (i.e. ectomycorrhiza). Other types of Mycorrhiza, such as ericoid, arbutoid, monotropoid and Orchid Mycorrhiza, are also encompassed within the term "Mycorrhiza" or "Mycorrhizae."

As used herein, the term "propagules" (ppg's) refers to any mycorrhizal material capable of forming symbiosis with plant roots, such as seeds, seedlings, growing agriculture or tree crops, clonal and micro propagated plants, and the like.

As used herein, the term "plant propagation material" refers to seeds and seedlings of all kinds (fruit, tubers, and grains), clonal and micro propagated plants, and the like.

As used herein, "improving" means that the plant has more of the specific quality than the plant would have had it if it had not been treated by methods of the present invention.

As used herein, the term "live" refers to an organism that can grow and or replicate.

As used herein, all numerical values relating to amounts, ratios, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

As used herein the term "10-34-0 fertilizer" refers to a liquid fertilizer containing about 10% nitrogen and about 34% polyphosphate.

In one embodiment the present invention is directed to a formulation comprising:
an active ingredient selected from the group consisting of mycorrhizae, *Bacillus amyloliquefaciens* and a mixture thereof;
propylene glycol; and
a stabilizer selected from the group consisting of benzenesulfonic acid, decyl (sulfophenoxy)-disodium salt, benzenesulfonic acid oxybis(decyl)-disodium salt mixture, sodium mono- and di-decyl disulfonated diphenyl oxide, D-glucopyranose, oligomeric, C9-11-alkyl glycosides and a mixture thereof.

In a preferred embodiment the active ingredient is mycorrhizae. In a more preferred embodiment, the mycorrhizae are live.

Mycorrhizae consortium may be present in formulations of the present invention at a concentration from about 0.1% to about 10% w/w, preferably form about 0.1% to about 1% w/w, more preferably from about 0.2% to about 0.3% w/w, and most preferably at about 0.25% or about 0.27% w/w.

In another preferred embodiment the active ingredient is *Bacillus amyloliquefaciens*. In a more preferred embodiment, the *B. amyloliquefaciens* is live.

*B. amyloliquefaciens* (technical powder concentrate with a nominal claim of $5 \times 10^{11}$ CFU/g) may be present in formulations of the present invention at a concentration from about 1% to about 10% w/w, preferably from about 1% to about 5% w/w, more preferably from about 2% to about 4% w/w and most preferably at about 3% w/w.

In a more preferred embodiment, the strain of *B. amyloliquefaciens* is BA-1.

In another preferred embodiment the active ingredient is a mixture of mycorrhizae and *B. amyloliquefaciens*.

Propylene glycol may be present in formulations of the present invention at a concentration from about 50% to about 97% w/w, preferably from about 70% to about 97% w/w, more preferably from about 80% to about 95% w/w, even more preferably from about 88% to about 93% w/w and most preferably at about 88.48%, about 88.75% or about 92.5% w/w.

Stabilizers may be present in formulations of the present invention at a concentration from about 1% to about 50% w/w, preferably from about 1% to about 20% w/w, more preferably from about 1% to about 10% w/w, even more preferably from about 4% to about 6% w/w and most preferably at about 5% w/w.

In another embodiment formulation of the present invention further comprise a viscosity enhancer selected from the group consisting of Bentone® 27V (organically modified hectorite clay), Bentone® 38 (organically modified hectorite clay), Bentone® 52 (organically modified montomorillonite clay), polyacrylic acid; carbomers; cellulose gums; Kelzan® xanthan gums, hydroxypropyl celluloses, Thixin® R (glyceryl tris 12-hydroxystearate) etcalkyl quaternary ammonium clay and a mixture thereof. In a preferred embodiment, the viscosity enhancer is alkyl quaternary ammonium clay.

Alkyl quaternary ammonium clay may be present in formulation of the present invention at a concentration from about 1% to about 10% w/w preferably from about 1% to about 5% w/w, even more preferably from about 2% to about 3.5% w/w, and most preferably at about 2.2% or 3.25% w/w.

In a preferred embodiment, the present invention is directed to agricultural formulations comprising:
an active ingredient selected from the group consisting of from about 0.1% to about 1% w/w mycorrhizae, from about 1% to about 5% w/w *Bacillus amyloliquefaciens* and a mixture thereof;
from about 70% to about 97% w/w propylene glycol;
from about 1% to about 20% w/w of a stabilizer selected from the group consisting of a stabilizer selected from the group consisting of benzenesulfonic acid, decyl (sulfophenoxy)-disodium salt, benzenesulfonic acid oxybis(decyl)-disodium salt mixture, sodium mono- and di-decyl disulfonated diphenyl oxide, D-glucopyranose, oligomeric, C9-11-alkyl glycosides and a mixture thereof; and
optionally, from about 1% to about 5% w/w of alkyl quaternary ammonium clay.

In a more preferred embodiment, the present invention is directed to an agricultural formulation comprising:
about 0.25% w/w mycorrhizae;
about 92.5% w/w propylene glycol;
about 5.0% w/w of a stabilizer selected from the group consisting of benzenesulfonic acid, decyl (sulfophenoxy)-disodium salt, benzenesulfonic acid oxybis (decyl)-disodium salt mixture, sodium mono- and di-decyl disulfonated diphenyl oxide, D-glucopyranose, oligomeric, C9-11-alkyl glycosides and a mixture thereof; and
about 2.2% w/w alkyl quaternary ammonium clay.

In another more preferred embodiment, the present invention is directed to an agricultural formulation comprising:
about 3.0% w/w *Bacillus amyloliquefaciens*;
about 88.75% w/w propylene glycol;
about 5.0% w/w of sodium mono- and di-decyl disulfonated diphenyl oxide; and
about 3.25% w/w alkyl quaternary ammonium clay.

In another more preferred embodiment, the present invention is directed to an agricultural formulation comprising:
about 0.27% w/w mycorrhizae;
about 3.0% w/w *Bacillus amyloliquefaciens*;
about 88.48% w/w propylene glycol;
about 5.0% w/w of sodium mono- and di-decyl disulfonated diphenyl oxide; and
about 3.25% w/w alkyl quaternary ammonium clay.

In another embodiment, formulations of the present invention may be mixed with a liquid fertilizer. In a preferred embodiment, the liquid fertilizer is selected from the group consisting of 10-34-0 fertilizer, 7-23-4+0.25 Zn fertilizer, 0-0-25+17% S fertilizer, 7-23-4 0.25 Zn fertilizer, 7-21-7 fertilizer and 6-24-6 fertilizer.

In a more preferred embodiment, the liquid fertilizer is a 10-34-0 fertilizer.

When liquid fertilizer is mixed with formulations of the present invention the liquid fertilizer may be present in the mix at a concentration from about 70% to about 99% v/v, preferably from about 80% to about 99% v/v, even more preferably from about 90% to about 99% v/v and most preferably at about 98% v/v, wherein the remainder of the mix comprises formulations of the present invention.

In a preferred embodiment the mix is a tank mix.

The formulations of the present invention including mixtures with liquid fertilizers can be applied by any convenient means. Those skilled in the art are familiar with the modes of application that include foliar applications such as spraying and soil applications including spraying, in-furrow treatments, or side-dressing.

Formulations of the present invention may be applied to any plant or plant propagation material thereof that may benefit from improved growth including agricultural crops, annual grasses, trees, shrubs, ornamental flowers and the like. Formulations of the present invention may further be applied to any area where a plant will grow including soil, a plant root zone and a furrow.

In another embodiment the present invention is further directed to a method of improving plant growth comprising applying formulations of the present invention to an area where a plant will grow.

In a preferred embodiment, the area where a plant will grow includes corn fields, cotton fields, peanut fields and soybean fields. In a more preferred embodiment, the area where a plant will grow includes corn fields, cotton fields and peanut fields.

In a preferred embodiment the area where a plant will grow is soil or a plant root zone.

In a more preferred embodiment, the soil is in the form of a furrow.

The formulations of the present invention may be applied at a rate of from about 5 to about 400 grams of mycorrhizae per hectare, preferably from about 10 to about 300 grams per hectare and more preferably from about 25 to about 300 grams per hectare.

The formulations of the present invention may be applied at a rate of from about 77 to about 310 grams of *B. amyloliquefaciens* per hectare, preferably from about 77 to about 231 grams per hectare and more preferably from about 77 to about 154 grams per hectare.

These representative embodiments are in no way limiting and are described solely to illustrate some aspects of the invention.

Further, the following example is offered by way of illustration only and not by way of limitation.

EXAMPLES

Garamite® 1958 is alkyl quaternary ammonium clay and is a registered trademark of and available from BYK Additives, Inc.

Dowfax® 3B2 surfactant and Dowfax® C10L surfactant also known as sodium mono- and di-decyl disulfonated diphenyl oxide are mixtures of 50% water, 38% benzenesulfonic acid, decyl(sulfophenoxy)-disodium salt (CAS #36445-71-3), 8% benzenesulfonic acid, oxybis(decyl)-di-sodium salt (CAS #70146-13-3) and 1.5% sulfuric acid disodium salt and are a registered trademark of and available from Dow Chemical Company.

Agnique® PG 9116 is D-glucopyranose, oligomeric, C9-11-alkyl glycosides (CAS #132778-08-6) and is a registered trademark of and available from BASF Corporation.

Agnique® AMD 3 L is dimethylamide of lactic acid and is available from BASF Corporation.

Klearfac® AA 270 (CAS #68649-29-6) is oxirane, methyl-, polymer with oxirane, mono-C10-C16-alkyl ethers, phosphates and is a registered trademark of and available from BASF Corporation.

Industrol® DF 204 (CAS #9003-11-6) is poloxalene and is a registered trademark of and available from BASF Corporation.

Example 1—Physical Compatibility of Various Surfactants at 10% v/v in 10-34-0 Fertilizer Method Various surfactants were added at 10% v/v to 10-34-0 fertilizer to determine physical stability. The surfactants were added and mixed and allowed to stand undisturbed.

Results

As seen in Table 1, below, only Dowfax® C10L, Dowfax® 3B2 and Agnique® PG 9116 provided clear solutions when added to 10-34-0 fertilizer.

TABLE 1

| | Physical compatibility of various surfactants at 10% v/v with 10-34-0 fertilizer | | | | | |
|---|---|---|---|---|---|---|
| | Dowfax® C10L | Dowfax® 3B2 | Klearfac® AA 270 | Industrol® DF 204 | Agnique® PG 9116 | Agnique® AMD 3L |
| Stability | Clear Solution | Clear Solution | Clear; Separation | Instant Separation | Clear Solution | Cloudy; Separation |

Example 2—Physical Compatibility of Mycorrhizae Formulations with 10-34-0 Fertilizer

TABLE 2

| Mycorrhizae formulations | | | |
|---|---|---|---|
| Formulation (% w/w) | M1 | M2 | M3 |
| Mycorrhizae Consortium | 0.25 | 0.25 | 0.25 |
| Propylene glycol | 92.55 | 92.55 | 92.55 |
| Garamite ® 1958 | 2.20 | 2.20 | 2.20 |
| Dowfax ® 3B2 Surfactant | 5.0 | — | — |
| Dowfax ® C10L Surfactant | — | 5.0 | — |
| Agnique ® PG 9116 Surfactant | — | — | 5.0 |

"ppg" denotes propagules

Mycorrhizae formulations of Table 2, above, were added and mixed at 2% v/v to 10-34-0 fertilizer to determine physical stability.

Results

As seen in FIG. 1, mixtures of each of M1-M3 with 10-34-0 fertilizer resulted in clear solutions for at least 1 hour.

Example 3—Physical Compatibility of *B. amyloliquefaciens* Formulation with 10-34-0 Fertilizer

TABLE 3

| *B. amyloliquefaciens* formulation | |
| --- | --- |
| Formulation (% w/w) | B1 |
| *B. amyloliquefaciens* BA-1 Technical Powder Concentrate | 3.0 |
| Propylene glycol | 88.75 |
| Garamite ® 1958 | 3.25 |
| Dowfax ® 3B2 Surfactant | 5.0 |

"ppg" denotes propagules
"CFU" denotes colony forming units

A *B. amyloliquefaciens* formulation containing strain BA-1 shown in Table 3, above, was added at 2% v/v to 10-34-0 fertilizer, mixed and allowed to stand undisturbed so as to determine physical stability.

Results

Figure 2:
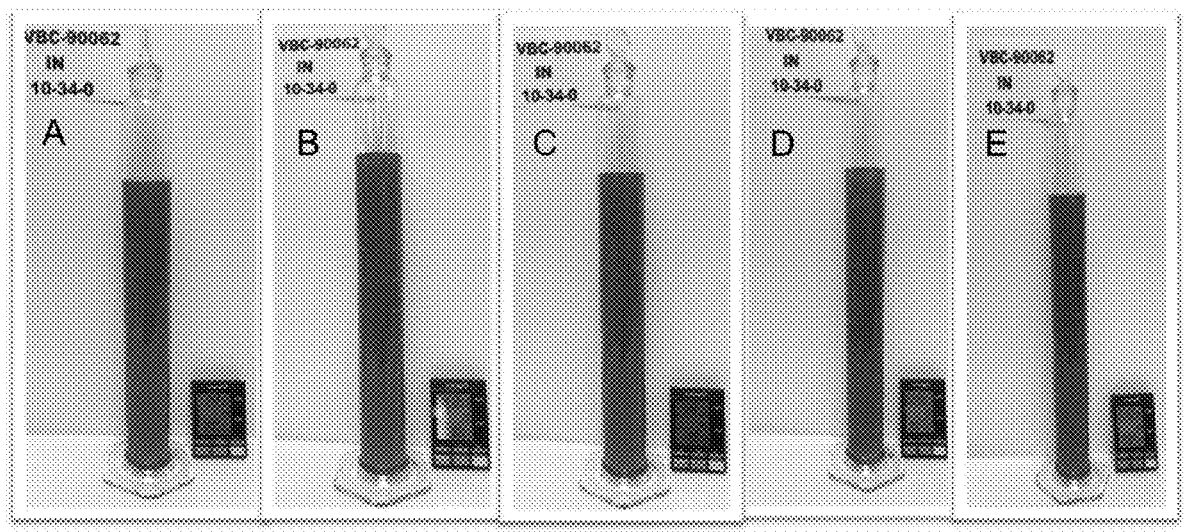
FIG. 2. Stability of formulation B1 at time 0 (A), 0.5 hours (B), 1 hour (C), 19 hours (D), and 19 hours following 3 inversions (E).

As seen in FIG. 2, the mixture of B1 with 10-34-0 fertilizer resulted in a clear liquid for at least 19 hours.

Example 4—Biological Stability of *B. amyloliquefaciens* and/or Mycorrhizae Formulations

TABLE 4

| Mycorrhizae and *B. amyloliquefaciens* formulation | |
| --- | --- |
| Formulation (% w/w) | MB1 |
| Mycorrhizae Consortium | 0.27 |
| *B. amyloliquefaciens* BA-1 Technical Powder Concentrate | 3.0 |
| Propylene glycol | 88.48 |
| Garamite ® 1958 | 3.25 |
| Dowfax ® 3B2 Surfactant | 5.0 |

"ppg" denotes propagules
"CFU" denotes colony forming units

Formulations B1 and MB1 of Tables 3 and 4, above, respectively, were subjected to 50, 25° and 30° C. temperatures for 3 months. Total colony forming units per gram were then recorded.

TABLE 5

| *B. amyloliquefaciens* count following 3-month incubation | | | | |
| --- | --- | --- | --- | --- |
| CFU/g | T = 0 | 5° C. | 25° C. | 30° C. |
| B1 | $8.71 \times 10^9$ | $8.73 \times 10^9$ | $8.37 \times 10^9$ | $9.41 \times 10^{10}$ |
| MB1 | $8.33 \times 10^9$ | $7.40 \times 10^9$ | $1.01 \times 10^{10}$ | $8.70 \times 10^9$ |

"CFU" denotes colony forming units

Results

As seen in Table 5, above, both formulations B1 and MB1 maintained a high concentration of viable *B. amyloliquefaciens* cells when tested at 3 months of storage at each of 50°, 25° and 30° C.

What is claimed is:

1. An agricultural formulation comprising:
    an active ingredient selected from the group consisting of mycorrhizae, *Bacillus amyloliquefaciens* and a mixture thereof;
    propylene glycol; and
    a stabilizer selected from the group consisting of benzenesulfonic acid, decyl (sulfophenoxy)-disodium salt, benzenesulfonic acid oxybis(decyl)-disodium salt mixture, sodium mono- and di-decyl disulfonated diphenyl oxide, D-glucopyranose, oligomeric, C9-11-alkyl glycosides and a mixture thereof.

2. The formulation of claim 1, further comprising alkyl quaternary ammonium clay.

3. The formulation of claim 1, wherein the *Bacillus amyloliquefaciens* is strain BA-1.

4. The formulation of claim 1, further comprising a liquid fertilizer.

5. The formulation of claim 4, wherein the liquid fertilizer is a 10-34-0 liquid fertilizer.

6. The formulation of claim 4, wherein the formulation comprises from about 80% to about 99% v/v of liquid fertilizer, wherein v/v denotes volume by total volume of the formulation.

7. An agricultural formulation comprising:
    an ingredient selected from the group consisting of about 0.1% to about 1% w/w mycorrhizae, from about 1% to about 5% w/w *Bacillus amyloliquefaciens* and a mixture thereof;
    from about 70% to about 97% w/w propylene glycol; and
    from about 1% to about 20% w/w of a stabilizer selected from the group consisting of benzenesulfonic acid, decyl (sulfophenoxy)-disodium salt, benzenesulfonic acid oxybis(decyl)-disodium salt mixture, sodium mono- and di-decyl disulfonated diphenyl oxide, D-glucopyranose, oligomeric, C9-11-alkyl glycosides and a mixture thereof, wherein w/w denotes weight by total weight of the formulation.

8. The formulation of claim 7, further comprising from about 1% to about 5% w/w of alkyl quaternary ammonium clay.

9. The formulation of claim 8, comprising:
    about 0.25% w/w mycorrhizae;
    about 92.5% w/w propylene glycol;
    about 5.0% w/w of a stabilizer selected from the group consisting of benzenesulfonic acid, decyl (sulfophenoxy)-disodium salt, benzenesulfonic acid oxybis (decyl)-disodium salt mixture, sodium mono- and di-decyl disulfonated diphenyl oxide, D-glucopyranose, oligomeric, C9-11-alkyl glycosides and a mixture thereof; and
    about 2.2% w/w alkyl quaternary ammonium clay.

10. The formulation of claim 8, comprising:
    about 3.0% w/w *Bacillus amyloliquefaciens;*
    about 88.75% w/w propylene glycol;
    about 5.0% w/w of sodium mono- and di-decyl disulfonated diphenyl oxide; and
    about 3.25% w/w alkyl quaternary ammonium clay.

11. The formulation of claim 8, comprising:
    about 0.27% w/w mycorrhizae;
    about 3.0% w/w *Bacillus amyloliquefaciens;*
    about 88.48% w/w propylene glycol;
    about 5.0% w/w of sodium mono- and di-decyl disulfonated diphenyl oxide; and
    about 3.25% w/w alkyl quaternary ammonium clay.

12. A tank mix comprising from about 1% to about 20% v/v of the formulation of claim 7 and from about 80% to about 99% v/v of a liquid fertilizer, wherein v/v denotes volume by total volume of the tank mix.

13. The tank mix of claim 12, wherein the liquid fertilizer is a 10-34-0 liquid fertilizer.

14. A method of improving plant growth comprising applying a formulation of claim 1 to an area where a plant will grow.

15. The method of claim 14, wherein the area where a plant will grow is soil.

16. The method of claim 15, wherein the soil is in the form of a furrow.

17. The method of claim 14, wherein the area where a plant will grow is a plant root zone.

* * * * *